United States Patent
Herzberg

(10) Patent No.: US 6,617,485 B2
(45) Date of Patent: Sep. 9, 2003

(54) BANDAGE FOR THE ANKLE JOINT

(75) Inventor: Thorsten Herzberg, Langenhorner Chaussee (DE)

(73) Assignee: Beiersdorf AG, Hamburg (DE)

( * ) Notice: Subject to any disclaimer, the term of this patent is extended or adjusted under 35 U.S.C. 154(b) by 0 days.

(21) Appl. No.: 09/915,837

(22) Filed: Jul. 26, 2001

(65) Prior Publication Data

US 2002/0035344 A1 Mar. 21, 2002

(30) Foreign Application Priority Data

Jul. 29, 2000 (DE) .......................... 100 37 342

(51) Int. Cl.⁷ ................................ A61F 13/00
(52) U.S. Cl. .............................. 602/41; 602/5; 602/23; 602/27
(58) Field of Search ............................. 602/5, 23, 27, 602/60–61, 65, 77; 128/871, 882

(56) References Cited

U.S. PATENT DOCUMENTS

| 3,508,544 A | 4/1970 | Moore et al. ............... 128/149 |
| 4,133,311 A | 1/1979 | Karczewski ................. 128/166 |
| 5,472,414 A | 12/1995 | Detty ........................... 602/27 |

FOREIGN PATENT DOCUMENTS

| DE | 42 91 109 | 4/1993 | ............. A61F/5/04 |

Primary Examiner—Nicholas D. Lucchesi
Assistant Examiner—Lalita M Hamilton
(74) Attorney, Agent, or Firm—Norris McLaughlin & Marcus

(57) ABSTRACT

A bandage 1 for the ankle joint, with a lower-leg part 20 and with a foot part 10 with two straps 11, 12, the lower-leg part 20 having at least one strap 21, 22, the foot part 10 having a first strap 11 on the medial side and a second strap 12 on the lateral side, the lower-leg part 20 and the foot part 10 being connected to one another in such a way that, when the bandage 1 is applied to the foot, the heel area is left open, and, with the bandage 1 applied, the lower-leg part 20 wraps round the posterior face of the lower leg in the distal lower-leg area and can be closed, particularly on the anterior face, and the foot part 10 lies under the sole and wraps round the foot with the medial strap 11 and the lateral strap 12, said straps 11, 12 starting from the plantar area, overlapping across the back of the foot and extending medially and laterally to the distal area of the lower leg.

2 Claims, 5 Drawing Sheets

BANDAGE FOR THE ANKLE JOINT

The invention describes a bandage for injuries to the ankle joint, for example distortions, mild sprains, extension injuries in the fibular area and the lateral ligament structure, and incipient degenerative changes of the upper and/or lower parts of the ankle joint.

BACKGROUND OF THE INVENTION

Depending on their design and on the indications for which they are intended, orthopedic bandages exert a fixing, guiding, bracing and/or supporting action on the extremities of the human body.

These medical bandages must have a shape which corresponds to the anatomical circumstances in order to be able to act externally on the human body with a form fit and a force fit.

Medical bandages of this kind are produced by cutting out blanks from planar material, for example neoprene, knitted fabrics or woven fabrics. The anatomically appropriate shape is obtained via the shape of the blanks or darts, for example with gussets, and subsequent joining together of the blanks, as is also customary in articles of clothing.

This joining together can be done by sewing, gluing or other conventional methods. The great disadvantage of these bandages is that the exact anatomical fit can be achieved only with difficulty and there are a large number of connection points, for example seams. These connection points change the properties of the material used, and there is the danger of pressure points on the skin.

Ankle joint ortheses or bandages are used preferably for the early functional treatment of recent fibular ligament ruptures and of mild and moderately severe tarsal distortions, and are also used in cases of chronic instability.

DE-A-38 40 714 discloses an ankle joint orthesis with a U-shaped support stirrup, the branches of which run together to form a bridge under the foot, reach upwards across the malleoli and are held together in their end region by a securing tape. The outer branch is in this case guided upward laterally in front of its malleolus, and the inner branch opposite the outer branch is guided upward in front of the Achilles tendon. Both branches, in the direction toward the bridge, are guided to a position in front of the heel, and, in the direction toward their ends, they extend upward in such a way that they ascend laterally along the lower-leg ridges and approximately parallel to these, and a holding tape is fitted in the lower area of the branches, which holding tape extends from the one branch obliquely upward across the instep to the other branch, and can be fastened thereon, engages above the malleoli about the Achilles tendon and, overlapping on the instep, ends on the other branch in a holding part. An ankle joint orthesis designed in this way is intended to prevent twisting, primarily in the lateral anterior direction, that is to say in the direction of a talipes equinus position. Since the U-shaped support stirrup of this ankle joint orthesis has its outer branch guided upward laterally in front of the malleolus and has its inner branch guided upward in front of the Achilles tendon, and is held together by a bridge running under the foot, the medial margin of the metatarsus is not gripped, with the result that the use of this ankle joint orthesis is limited.

DE-A-39 09 922 describes a foot fixation splint. This foot fixation splint is used in particular for the postoperative treatment of an injured ankle joint, with a foot part which surrounds the foot and to which there is joined a holding part extending upward into the calf area and provided with closure straps. The holding part is in this case divided into two side parts which are joined to the foot part and are of cup-shaped design. The area of each side part covering the malleolus is provided with a window-type recess. The area of the Achilles tendon on the foot part and on the holding part is in this case left open. The adjustable and fixable tape-like closure straps are made of an inextensible material, and one closure strap is arranged on the foot part in such a way that it engages over the back of the foot and so fixes the first radius of the metatarsus against supinatory elevation. A foot fixation splint of this kind is intended, on the one hand, to ensure a satisfactory immobilization of the foot that is to be treated, and, on the other hand, to avoid the disadvantages of a plaster cast, since after injuries and operations involving the external ligament apparatus the foot is often put in plaster in order to immobilize it, and postoperative treatment of operation wounds is not possible on account of a great many serious disadvantages. In the case of this foot fixation splint, the starting point is a U-shaped joint cuff with a full-surface sole part which covers the middle and front portions of the foot as far as the ball of the small toe, but which does not provide sufficient suppleness in the metatarsal area.

DE-C-43 18 588 likewise discloses an ankle joint orthesis consisting of a U-shaped joint cuff which is made of thermoplastic material and is composed of an outer malleolar splint and an inner malleolar splint. These malleolar splints are connected via a bridge running underneath the heel. The malleolar splints additionally have anatomically correct depressions for adaptation to the malleolar contours and for a correct anatomical fit. A further element of the orthesis is its metatarsal part, which is likewise made of thermoplastic material. This part of the orthesis runs obliquely under the sole of the foot, proximal to the capitula of metatarsals I–V, and is formed into a loop shape medially and laterally. The loops thus formed enclose the outer and inner margins of the foot. They guide the metatarsus on the one hand, and on the other hand serve for securing cross and transverse belts. The metatarsal part is in this case connected on the sole side by a bridge which is again made of thermoplastic material but is highly flexible. This bridge has the function of an articulation and acts analogously to an integral hinge. The pivot axis of this articulation formed in the highly flexible bridge runs from dorsomedial to anterolateral and forms with the long axis of the foot an angle of approximately 10°, in accordance with the anatomy of the lower part of the ankle joint.

DE 42 91 109 C2 discloses a support device for an ankle joint with a closable main support body, which has a lower-leg part and a foot part, and with an inner and/or outer support part in each case fitted on a side part of the main support body, the lower-leg part and the foot part being perpendicular to each other. The support parts are arranged on the main support body in such a way that they can be removed from it. Both the lower-leg part and the foot part have velcro-type fasteners which can be closed in order to apply the support device.

At their end toward the sole of the foot, the support parts also have the possibility of being connected via a connecting tape which runs under the sole. Finally, the foot part has at least one stretchable tape which is secured at one end on the outside of the sole area and can be guided away from the sole area via the back of the foot in order to be wound in a spiral formation around the lower-leg area.

It is an object of the invention to design a bandage which has a high degree of functionality with proprioceptive action, but which at the same time is easy and uncomplicated for the patient to apply and which, by means of dispensing with rigid elements, offers a high degree of dynamics. Moreover, the bandage should be inexpensive to produce.

This object is achieved by the bandage defined in accordance with the main claim. The subclaims relate to advantageous developments of the bandage.

SUMMARY OF THE INVENTION

Accordingly, the invention relates to a bandage for the ankle joint with a lower-leg part and with a foot part with two straps.

The lower-leg part has at least one strap, and the foot part has a first strap on the medial side and a second strap on the lateral side.

According to the invention, the lower-leg part and the foot part are connected to one another, in particular by sewing, in such a way that, when the bandage is applied to the foot, the heel area of the foot is left open.

DETAILED DESCRIPTION

With the bandage applied, the lower-leg part wraps round the posterior face of the lower leg in the distal lower-leg area and can be closed, particularly on the anterior face. The foot part lies under the sole and wraps round the foot with the medial and lateral straps, said straps, starting from the plantar area, overlapping across the back of the foot and extending medially and laterally to the distal area of the lower leg.

In a first preferred embodiment of the bandage, a connection part is connected, once again preferably sewn, to the lower-leg part and to the foot part, and, with the bandage applied, the connection part wraps round the anterior face of the lower leg in the distal lower-leg area and the dorsal face of the foot.

The connection part gives the bandage a tubular configuration, with the result that the bandage can be securely applied and positioned in the anterior area of the lower leg and in the dorsal area of the foot and treatment reliability is thereby enhanced.

The lower-leg part also preferably has a medial strap and a lateral strap which wrap round the posterior face of the lower leg in a circle and are closed on the anterior face.

In a further preferred embodiment, the lower-leg part and the foot part of the bandage are made of a material which is laminated at least on both sides and which has a VELCRO®-like velour on the outside and a skin-compatible textile material on the inside.

Moreover, spacer fabrics with corresponding laminations can be used or, in the case of technical machine finishing, also without laminations.

Such spacer fabrics are disclosed in EP 0 071 212 B1. Spacer fabrics are mat-like laminated articles with a top layer of nonwoven fiber or filament, a bottom layer, and, between these layers, individual or clustered holding fibers which, distributed across the surface of the laminated article, are needled through the particle layer and join the top layer and the bottom layer together. In an additional feature according to EP 0 071 212 B1, but not an essential one, particles of inert stone, for example sand, gravel or the like, are provided in the holding fibers.

The holding fibers needled through the particle layer maintain the top layer and the bottom layer at a distance from each other and they are connected to the top layer and the bottom layer.

Woven or knitted spacer materials are described inter alia in two articles, namely:

an article from the specialist journal "kettenwirk-praxis 3/93", 1993, pages 59 to 63 "Raschelgewirkte Abstandsgewirke" [Raschel-knit spacers] and an article from the specialist journal "kettenwirk-praxis 1/94", 1994, pages 73 to 76 "Raschelgewirkte Abstandsgewirke" [Raschel-knit spacers]

and reference is hereby made to their content, and their content is part of this disclosure and invention.

Other, preferred materials are neoprene foam, polyurethane foam or polyester foam, and these are preferably perforated for better aeration.

In a further preferred embodiment of the bandage, the material has an elasticity of 30 to 150% in the X axis and of 5 to 70% in the Y axis, where the X axis runs in a circle round the lower leg and foot respectively in the applied state of the bandage, and the Y axis, again in the applied state of the bandage, runs vertically in the lower-leg part, i.e. longitudinally, and follows the longitudinal axis of the foot in the foot part.

In a further preferred embodiment of the bandage, the material for the connection part has an elasticity of 50 to 200% in the X axis and of 0 to 50% in the Y axis, where the X axis runs in a circle or horizontally round the lower leg and foot respectively in the applied state of the bandage, and the Y axis, again in the applied state of the bandage, runs vertically in the lower-leg part, i.e. longitudinally, and follows the longitudinal axis of the foot in the foot part.

Finally, an excellent configuration of the bandage is obtained if the lower-leg part or the straps on the lower-leg part and/or the straps of the foot part have VELCRO® hook and loop fasteners or press studs.

The circular arrangement in the distal area of the lower leg leads to an individually adjustable compression effect and follows the course of the anterior and posterior tibiofibular ligaments, the fibrous bands holding the tibia and fibula together and thereby supporting them.

The arrangement round the foot, formed by a medial strap and a lateral strap each starting from the plantar area and overlapping on the back of the foot and extending to the distal area of the lower leg, has a stabilizing effect on the upper and lower parts of the ankle, as active supination and pronation of the foot is limited and thus inversion of the foot is reduced. This has an advantageous effect on the lateral fibulocalcaneal ligament structure since eversion tends to damage this structure. As the straps of the arrangement round the foot are individually adjustable, it is possible to set the strength of support to meet the particular indication. The arrangement round the foot follows the anatomy of the so-called stirrup which is formed by the tendons of the anterior lower-leg muscle and the long peroneal muscle.

The bandage places hardly any restriction on the physiological gait pattern. The opening left in the heel area means that the risk of pressure points in the heel contact area is avoided and the sensation of contact with the ground is maintained.

The invention is explained in more detail with reference to five diagrammatic drawings of an illustrative embodiment, specifically the configuration for the right foot, without this implying any unnecessary limitation on the invention. The embodiment of the bandage for the left foot is the mirror image of the former.

BRIEF DESCRIPTION OF THE DRAWINGS

In the drawings:

FIG. 1 represents the blanks for the foot part 10 and for the lower-leg part 20 of an excellent configuration of bandage 1 for the ankle joint.

Figure 1:
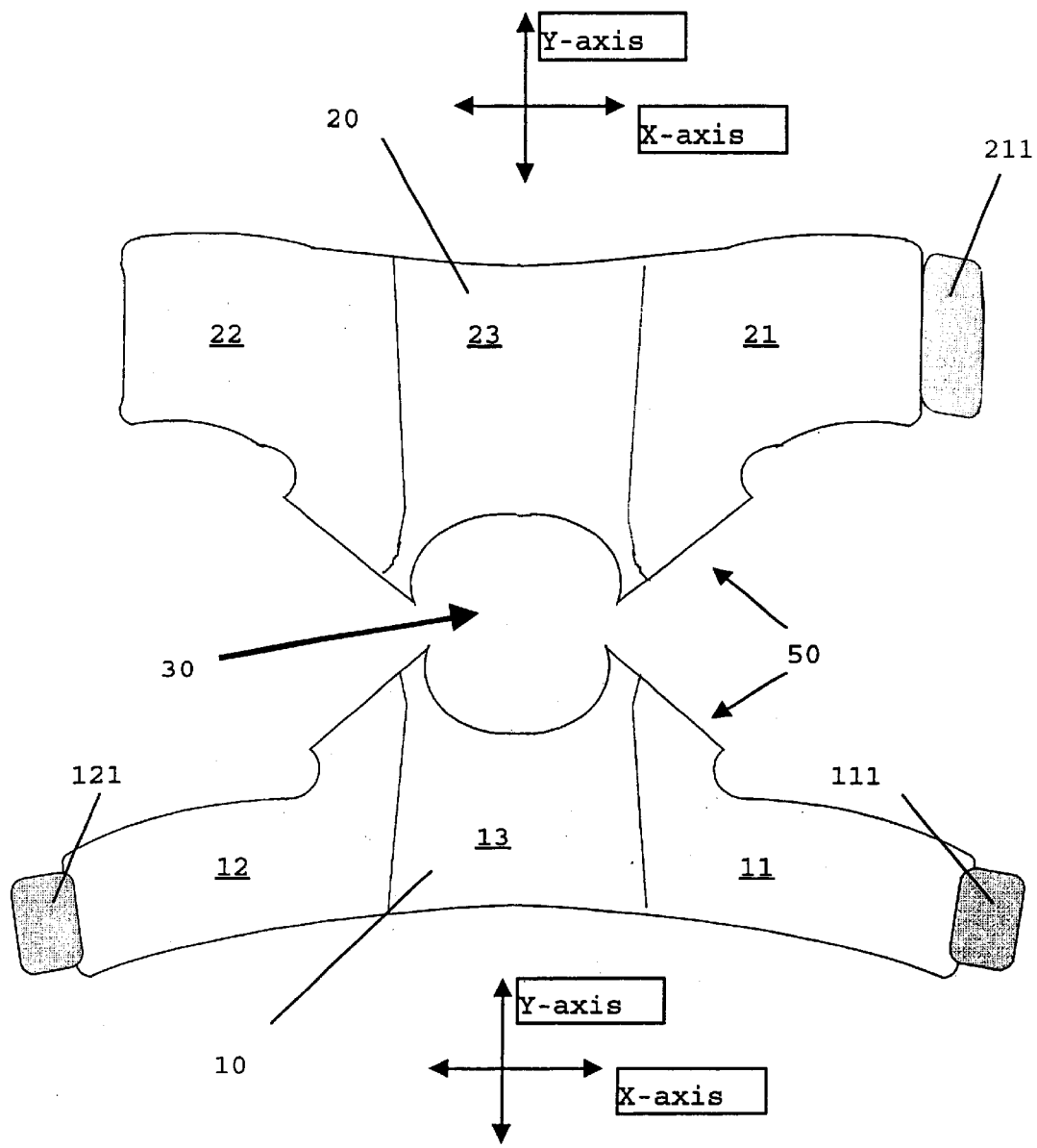
FIG. 1 shows the blank for a particularly advantageous embodiment of the bandage, with the lower-leg part and the foot part separated.

The lower-leg part 20 consists of a central portion 23 which has a basic rectangular shape, the edge of the central portion 23 having a rounded cutout in the heel area. Two straps 21, 22 are integrally formed on the central portion 23. The strap 22 additionally has a velcro tongue 23 which ensures closure of the lower-leg part 20 when the bandage 1 is applied.

The foot part 10 has a medial strap 11 on the medial side and a lateral strap 12 on the lateral side, which straps for their part are joined to one another via a central portion 13. The central portion 13 is likewise substantially rectangular, except that the edge of the central portion 13 in the heel area has a rounded cutout.

A tongue 111, 121 is secured respectively on the medial strap 11 and on the lateral strap 12, and these tongues are preferably designed in such a way that the straps 11, 12 are fixed in their position by a velcro fastening.

Delta-shaped extensions are formed on the straps 21, 22 of the lower-leg part 20 and on the straps 11, 12 of the foot part 10, and these extensions each run out in a single edge. Two of the edges are in each case connected to one another, in particular sewn to one another, resulting in two seams 50. The extensions are also configured in such a way that the lower-leg part 20 and the foot part 10 are connected to one another in such a way that when the bandage 1 is applied to the foot the heel area lies in a cutout 30, and the central portion 23 of the lower-leg part 20 and the central portion 13 of the foot part 10 have an angle of approximately 90° after they have been sewn.

Figure 2:
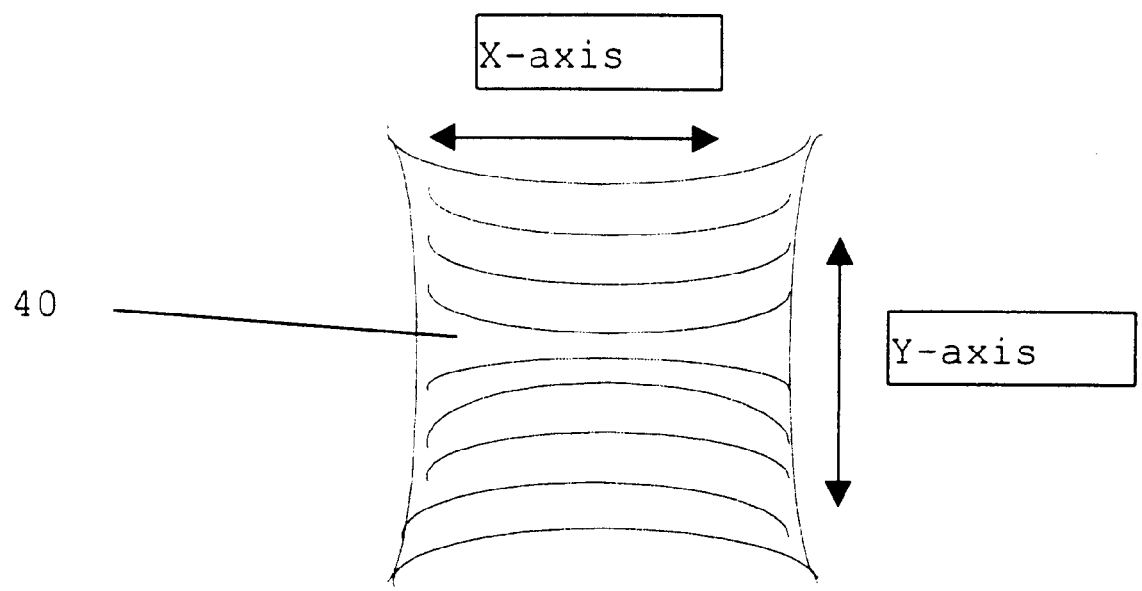
FIG. 2 shows the blank for the preferably used connection part.

FIG. 2 shows the blank for the optionally used connection part 40. This is substantially of rectangular shape and is connected in the area of the central portions 13, 23 to the lower-leg part 20 and foot part, respectively, and in this case sewing is again particularly preferred.

Figure 3:
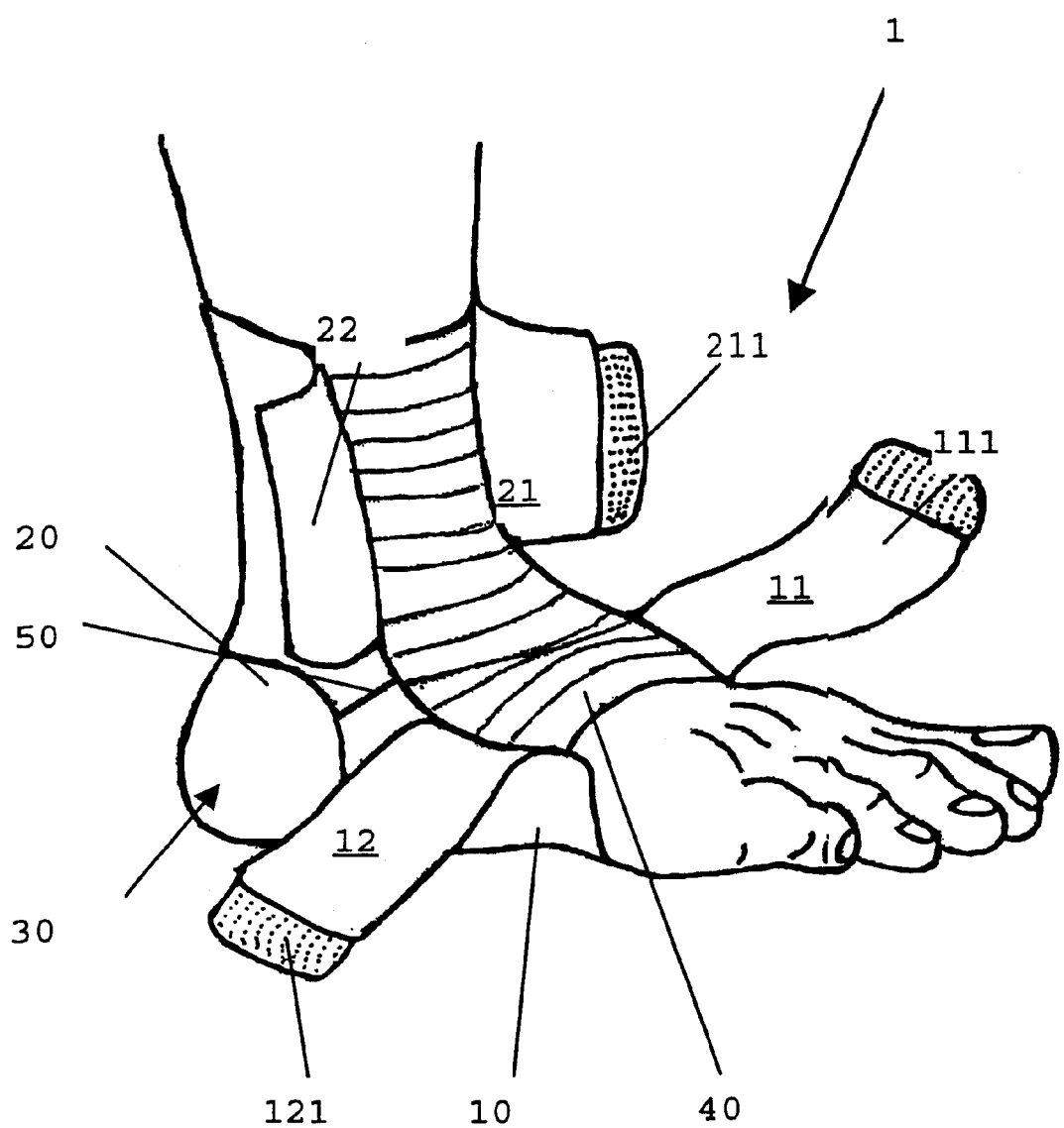
FIG. 3 shows the applied bandage, without the straps being closed.

FIG. 3 shows the applied bandage 1, without the straps 11, 12, 21, 22 being closed. In the distal area of the lower leg, the lower-leg part 20 wraps round the posterior face of the lower leg in a circle and can be closed on the anterior face. The foot part 10 lies under the sole of the foot and wraps round the foot with the medial strap 11 and the lateral strap 12.

In the distal area of the lower leg, the connection part 40 wraps round the anterior face of the lower leg and the dorsal face of the foot.

Figure 4:
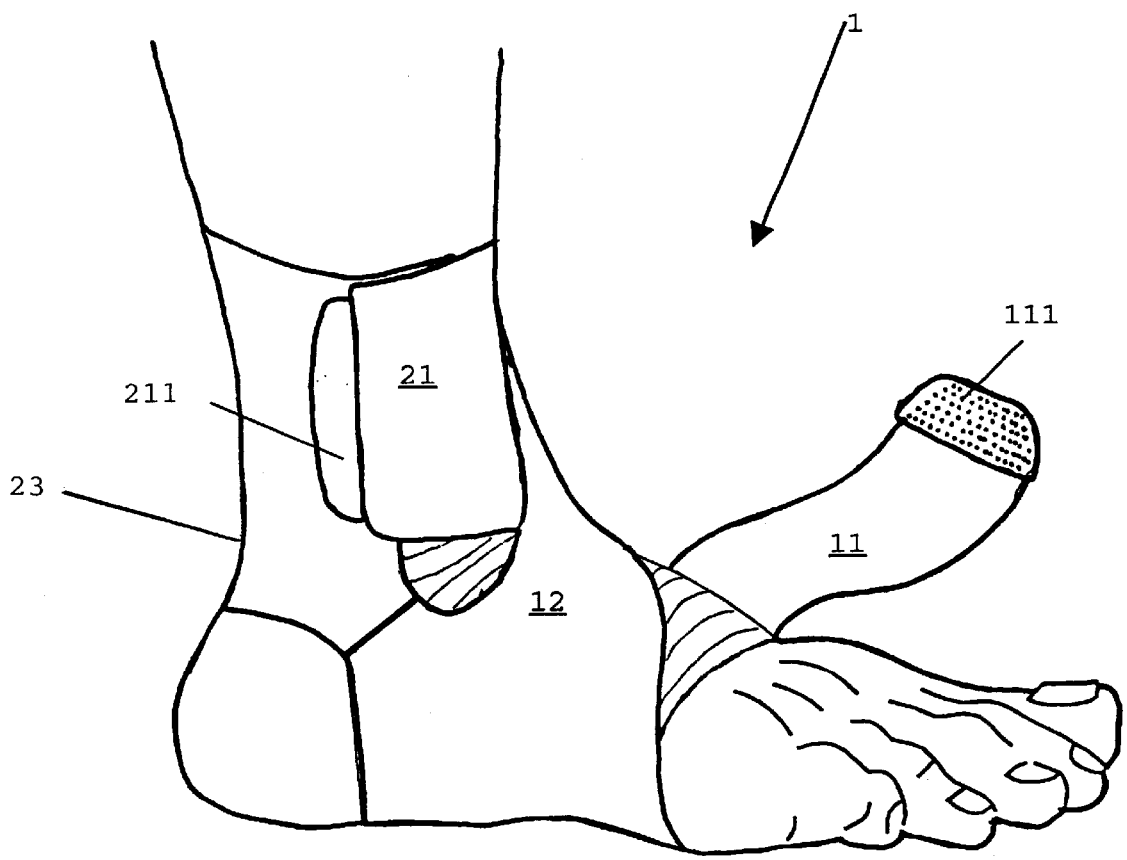
FIG. 4 shows the bandage half applied, with some of the straps closed.
Figure 5:
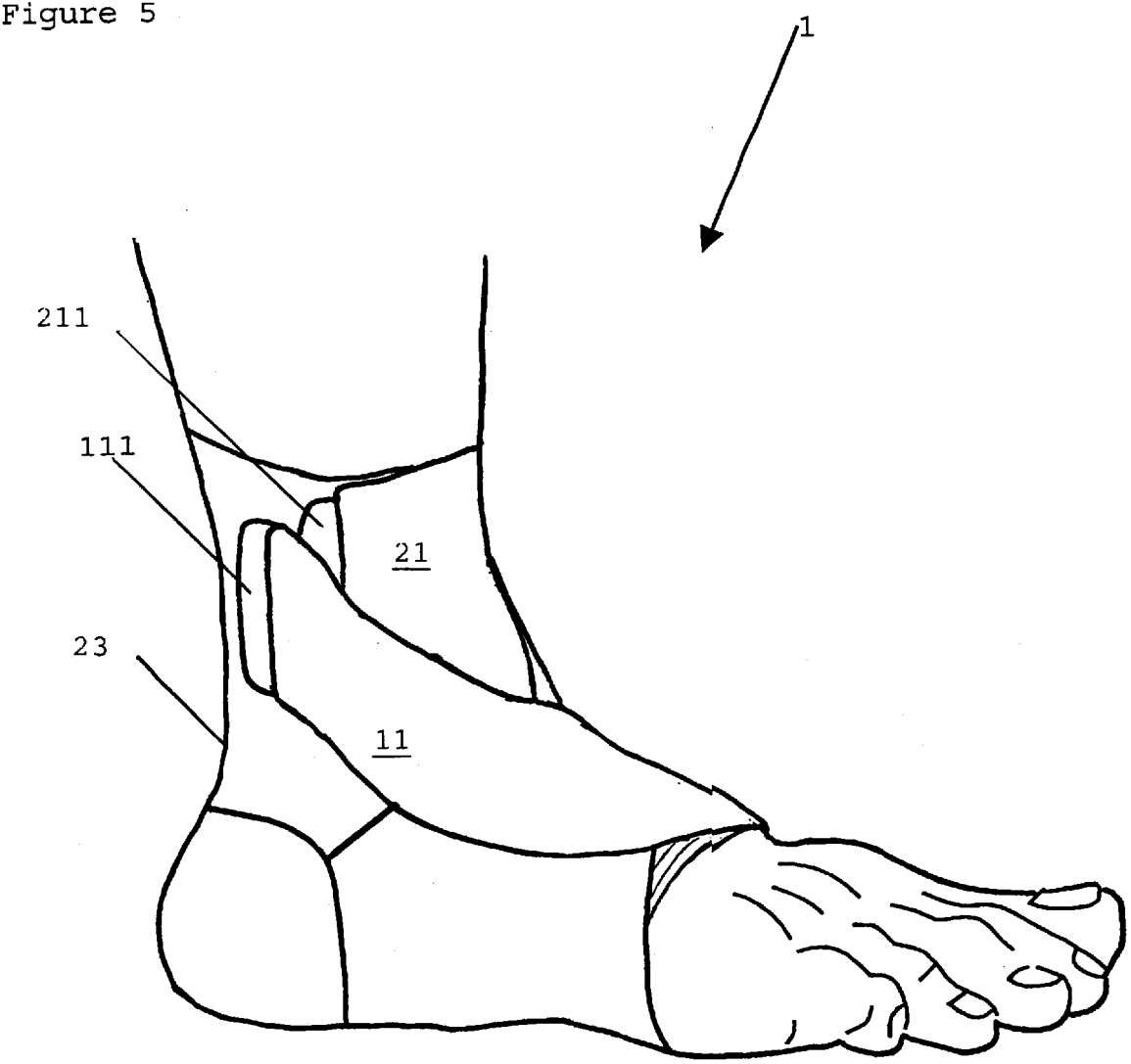
FIG. 5 shows the applied bandage.

FIGS. 4 and 5 show the procedure for closing the bandage 1.

The straps 21, 22 of the lower-leg part 20 are passed round the lower leg, the medial strap 22 being held on the lateral strap 21 by the velcro-type tongue 23.

The foot part 10 is then closed. The straps 11, 12 of the foot part 10 start from the plantar area, overlap across the back of the foot and extend medially and laterally to the distal area of the lower leg. The straps 11, 12 are fixed on the bandage 1 itself by means of the tongues 111, 121.

I claim:

1. A bandage for the ankle joint, comprising a lower-leg part and a foot part, the lower-leg part having a medial side and a lateral side at least one of which sides is extended to form a strap, the foot part having a medial side and a lateral side, said sides each being extended to form a medial strap on the medial side and a lateral strap on the lateral side, the lower-leg part and the foot part being connected to one another such that, when the bandage is applied to the foot, the heel area is left open, and, with the bandage applied, the lower-leg part wraps around the posterior face of the lower leg in the distal lower-leg area and can be closed, and the foot part lies under the sole and wraps round the foot with the medial strap and lateral strap, said straps being adapted to, when applied to the foot and starting from the plantar area, overlap across the back of the foot and extend medially and laterally to the distal area of the lower leg, wherein the bandage is made of a material which has an elasticity of 30 to 150% in the X axis and of 5 to 70% in the Y axis, where the X axis runs in a circle round the lower leg and foot respectively in the applied state of the bandage, and the Y axis, in the applied state of the bandage, runs vertically in the lower-leg part, and follows the longitudinal axis of the foot in the foot part.

2. The bandage as claimed in claim 1, wherein a connection part is connected to the lower-leg part and to the foot part, and, with the bandage applied, the connection part wraps round the anterior face of the lower leg in the distal lower-leg area and wraps round the dorsal face of the foot and the connection part is made of a material having an elasticity of 50 to 200% in the X axis and of 0 to 50% in the Y axis, where the X axis runs in a circle round the lower leg and foot respectively in the applied state of the bandage, and the Y axis, in the applied state of the bandage, runs vertically in the lower-leg part, and follows the longitudinal axis of the foot in the foot part.

* * * * *